(12) United States Patent
Nau, Jr. et al.

(10) Patent No.: US 8,388,647 B2
(45) Date of Patent: Mar. 5, 2013

(54) APPARATUS FOR TISSUE SEALING

(75) Inventors: William H. Nau, Jr., Longmont, CO (US); Joe D. Sartor, Longmont, CO (US)

(73) Assignee: Covidien LP, Mansfield, MA (US)

( * ) Notice: Subject to any disclaimer, the term of this patent is extended or adjusted under 35 U.S.C. 154(b) by 642 days.

(21) Appl. No.: 12/607,191

(22) Filed: Oct. 28, 2009

(65) Prior Publication Data
US 2011/0098689 A1 Apr. 28, 2011

(51) Int. Cl.
A61B 17/00 (2006.01)
(52) U.S. Cl. ....................................... 606/207
(58) Field of Classification Search ............ 606/52, 606/169, 205, 207
See application file for complete search history.

(56) References Cited

U.S. PATENT DOCUMENTS

| | | | |
|---|---|---|---|
| 3,862,630 A | 1/1975 | Balamuth | |
| D263,020 S | 2/1982 | Rau, III | |
| D295,893 S | 5/1988 | Sharkany et al. | |
| D295,894 S | 5/1988 | Sharkany et al. | |
| 5,282,799 A | 2/1994 | Rydell | |
| D348,930 S | 7/1994 | Olson | |
| 5,334,183 A | 8/1994 | Wuchinich | |
| 5,383,897 A | 1/1995 | Wholey | |
| 5,558,672 A | 9/1996 | Edwards et al. | |
| 5,569,241 A | 10/1996 | Edwardds | |
| 5,599,350 A * | 2/1997 | Schulze et al. | 606/51 |
| D384,413 S | 9/1997 | Zlock et al. | |
| 5,707,369 A | 1/1998 | Vaitekunas et al. | |
| 5,755,717 A * | 5/1998 | Yates et al. | 606/51 |
| 5,941,869 A | 8/1999 | Patterson et al. | |
| 6,004,335 A | 12/1999 | Vaitekunas et al. | |
| 6,024,743 A | 2/2000 | Edwards | |
| D424,694 S | 5/2000 | Tetzlaff et al. | |
| D425,201 S | 5/2000 | Tetzlaff et al. | |
| 6,066,139 A | 5/2000 | Ryan et al. | |
| 6,099,537 A | 8/2000 | Sugai | |
| 6,267,761 B1 | 7/2001 | Ryan | |
| D449,886 S | 10/2001 | Tetzlaff et al. | |
| D457,958 S | 5/2002 | Dycus et al. | |
| D457,959 S | 5/2002 | Tetzlaff et al. | |
| 6,461,352 B2 | 10/2002 | Morgan et al. | |
| 6,485,489 B2 | 11/2002 | Teirstein et al. | |
| 6,743,239 B1 | 6/2004 | Kuehn et al. | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

International Search Report EP10189206 dated Mar. 17, 2011.

(Continued)

*Primary Examiner* — Linda Dvorak
*Assistant Examiner* — Jocelyn D Ram

(57) ABSTRACT

An ultrasound forceps for sealing tissue is provided. The forceps includes one or more shaft members having an end effector assembly disposed at a distal end thereof. The end effector assembly includes opposing jaw members movable from a first position in spaced relation relative to another subsequent position wherein the jaw members cooperate to grasp tissue therebetween. One or both of the jaw members includes an ultrasound transducer coupled to an ultrasound generator adapted to provide an electrical signal to the ultrasound transducer to induce treatment pulses therein.

12 Claims, 5 Drawing Sheets

U.S. PATENT DOCUMENTS

| | | | |
|---|---|---|---|
| D493,888 S | 8/2004 | Reschke | |
| 6,773,409 B2 * | 8/2004 | Truckai et al. | 601/2 |
| D496,997 S | 10/2004 | Dycus et al. | |
| D499,181 S | 11/2004 | Dycus et al. | |
| 6,932,810 B2 | 8/2005 | Ryan | |
| D509,297 S | 9/2005 | Wells | |
| 6,958,070 B2 | 10/2005 | Witt et al. | |
| 6,977,495 B2 | 12/2005 | Donofrio | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,244,257 B2 | 7/2007 | Podjahsky et al. | |
| 7,270,660 B2 | 9/2007 | Ryan | |
| D564,662 S | 3/2008 | Moses et al. | |
| 7,338,526 B2 | 3/2008 | Steinberg | |
| D567,943 S | 4/2008 | Moses et al. | |
| 7,361,172 B2 * | 4/2008 | Cimino | 606/27 |
| 7,396,336 B2 | 7/2008 | Orszulak et al. | |
| D575,395 S | 8/2008 | Hushka | |
| D575,401 S | 8/2008 | Hixson et al. | |
| 8,267,936 B2 * | 9/2012 | Hushka et al. | 606/51 |
| 8,277,447 B2 * | 10/2012 | Garrison et al. | 606/51 |
| 2002/0165469 A1 | 11/2002 | Murakami | |
| 2003/0018270 A1 * | 1/2003 | Makin et al. | 600/466 |
| 2003/0069570 A1 | 4/2003 | Witzel et al. | |
| 2003/0191396 A1 * | 10/2003 | Sanghvi et al. | 600/476 |
| 2004/0054364 A1 * | 3/2004 | Aranyi et al. | 606/27 |
| 2004/0064151 A1 | 4/2004 | Mollenauer | |
| 2004/0176756 A1 | 9/2004 | McGaffigan | |
| 2004/0210282 A1 | 10/2004 | Flock et al. | |
| 2005/0033278 A1 | 2/2005 | McClurken et al. | |
| 2005/0261588 A1 * | 11/2005 | Makin et al. | 600/459 |
| 2007/0043352 A1 * | 2/2007 | Garrison et al. | 606/51 |
| 2007/0173813 A1 * | 7/2007 | Odom | 606/51 |
| 2007/0265620 A1 | 11/2007 | Kraas | |
| 2008/0004616 A1 | 1/2008 | Patrick | |
| 2008/0319442 A1 | 12/2008 | Unger et al. | |
| 2009/0275865 A1 * | 11/2009 | Zhao et al. | 601/2 |
| 2011/0004210 A1 * | 1/2011 | Johnson et al. | 606/46 |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 20 2007 009317 | 10/2007 |
| DE | 19738457 | 1/2009 |
| EP | 1159926 | 12/2001 |
| EP | 0774232 | 1/2005 |
| EP | 1787597 | 5/2007 |
| JP | 61-501068 | 9/1984 |
| JP | 6-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 02085218 | 10/2002 |
| WO | WO 03/090630 | 11/2003 |
| WO | WO 2004/073753 | 9/2004 |
| WO | WO 2005/110264 | 11/2005 |
| WO | WO 2007082422 A1 * | 7/2007 |

OTHER PUBLICATIONS

U.S. Appl. No. 12/244,873, filed Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/249,263, filed Oct. 10, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.
U.S. Appl. No. 12/353,470, filed Jan. 14, 2009.
U.S. Appl. No. 12/353,474, filed Jan. 14, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/621,056, filed Nov. 18, 2009.
U.S. Appl. No. 12/690,726, filed Jan. 20, 2010.
U.S. Appl. No. 12/692,414, filed Jan. 22, 2010.
U.S. Appl. No. 12/692,810, filed Jan. 25, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/710,033, filed Feb. 22, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1965), British Medical Journal Feb. 6, 1976, vol. 1, No. 5431 p. 361, ISSN: 0007-1447.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.

Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/18676 dated Sep. 19, 2003.
Int'l Search Report PCT/US03/28534dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Johnson et al. "Evaluation of the LigaSure™ Vessel Sealing System in Hemorrhoidectomy" American College of Surgeons (ACS) Clinical Congress Poster (2000).
Paul G. Horgan, "A Novel Technique for Parenchymal Division During Hepatectomy" The American Journal of Surgery, vol. 181, No. 3, Apr. 2001 pp. 236-237.
Int'l Search Report EP 06006716.2 dated Aug. 4, 2006.

* cited by examiner

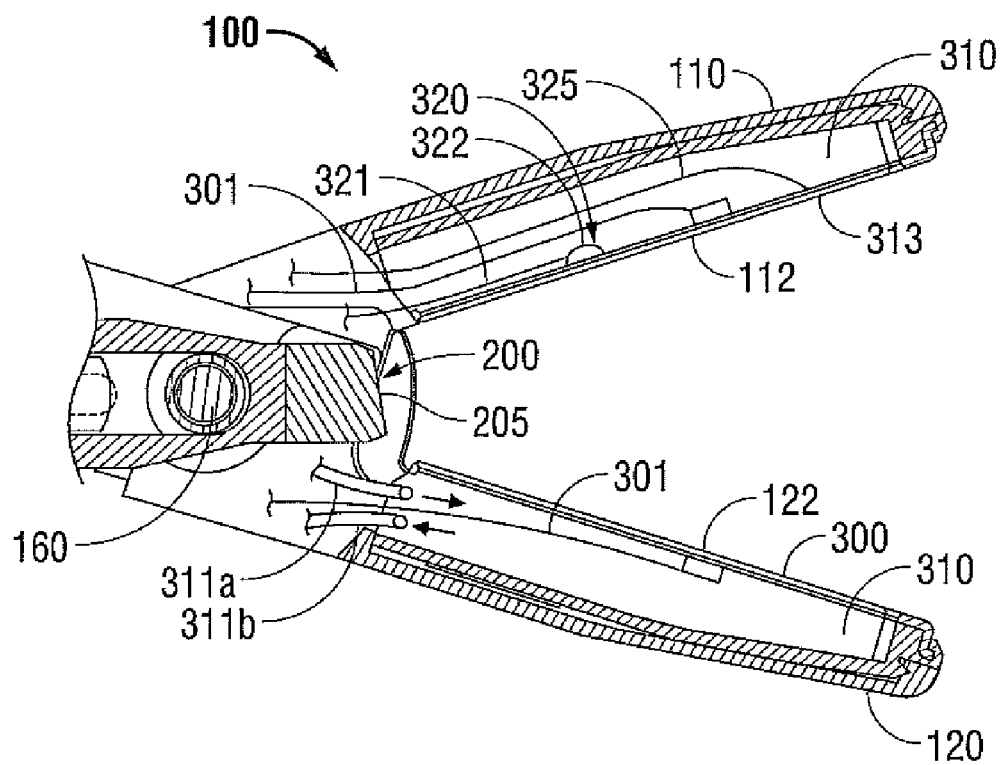
FIG. 3
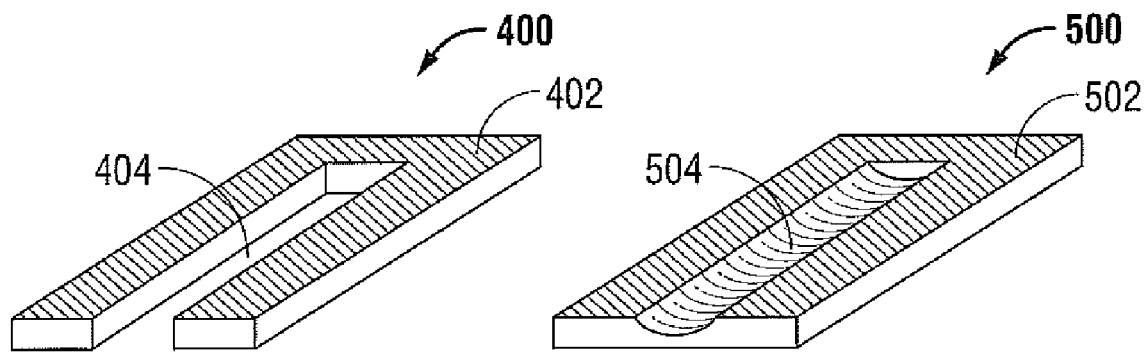
FIG. 4
FIG. 5

US 8,388,647 B2

APPARATUS FOR TISSUE SEALING

BACKGROUND

1. Technical Field

The present disclosure relates to forceps for sealing various types of tissue. More particularly, the present disclosure relates to open, laparoscopic or endoscopic forceps that utilize ultrasound energy to seal tissue.

2. Description of the Related Art

In many surgical procedures, body vessels, e.g., blood vessels, ducts, adhesions, fallopian tubes, etc. are sealed to defunctionalize or close the vessel. Traditionally, staples, clips or sutures have been used to close a body vessel. However, these traditional procedures often leave foreign body material inside a patient. In an effort to reduce foreign body material left within the patient and to more effectively seal the body vessel, energy techniques that seal by heat processes have been employed.

A forceps is particularly useful for sealing tissue and vessels since forceps utilizes mechanical action to constrict, grasp, dissect and/or clamp tissue. Current vessel sealing procedures utilize heat treatment to heat and desiccate tissue causing closure and sealing of the body vessel. In addition, forceps allow for control of the applied pressure to the tissue. The combination of heating and applied pressure provides a uniform, controllable seal and that is capable of providing such a seal with minimum collateral damage to body tissue.

SUMMARY

According to one aspect of the present disclosure, an ultrasound forceps for sealing tissue is provided. The forceps includes one or more shaft members having an end effector assembly disposed at a distal end thereof. The end effector assembly includes opposing jaw members movable from a first position in spaced relation relative to another subsequent position wherein the jaw members cooperate to grasp tissue therebetween. One or both of the jaw members includes an ultrasound transducer coupled to an ultrasound generator adapted to provide an electrical signal to the ultrasound transducer to induce treatment pulses therein.

A method for sealing tissue is also contemplated by the present disclosure. The method includes an initial step of providing an ultrasound forceps including an end effector assembly having opposing jaw members. One or both of the jaw members includes an ultrasound transducer. The method also includes the step of supplying an electrical signal to the ultrasound transducer to induce vibrations therein.

According to another aspect of the present disclosure, an ultrasound forceps for sealing tissue is provided. The forceps includes one or more shaft members having an end effector assembly disposed at a distal end thereof. The end effector assembly includes opposing jaw members movable from a first position in spaced relation relative to another subsequent position wherein the jaw members cooperate to grasp tissue therebetween. Each of the jaw members includes a plurality of ultrasound transducers coupled to an ultrasound generator adapted to provide an electrical signal to the plurality of ultrasound transducers to induce treatment pulses therein. The treatment pulses induce heating and provide localized transient pressures in combination with sustained jaw pressure by the opposing jaw members to bond tissue elements and/or tissue polymer chains resulting in joining of tissue surfaces or formation of anatomical lumens.

BRIEF DESCRIPTION OF THE DRAWINGS

Various embodiments of the present disclosure are described herein with reference to the drawings wherein:

FIG. 3 is cross-sectional side view of an ultrasound end effector assembly according to one embodiment of the present disclosure;

FIG. 4 is a perspective view of an ultrasound transducer according to one embodiment of the present disclosure;

FIG. 5 is a perspective view of an ultrasound transducer according to another embodiment of the present disclosure;

DETAILED DESCRIPTION

Figure 1:
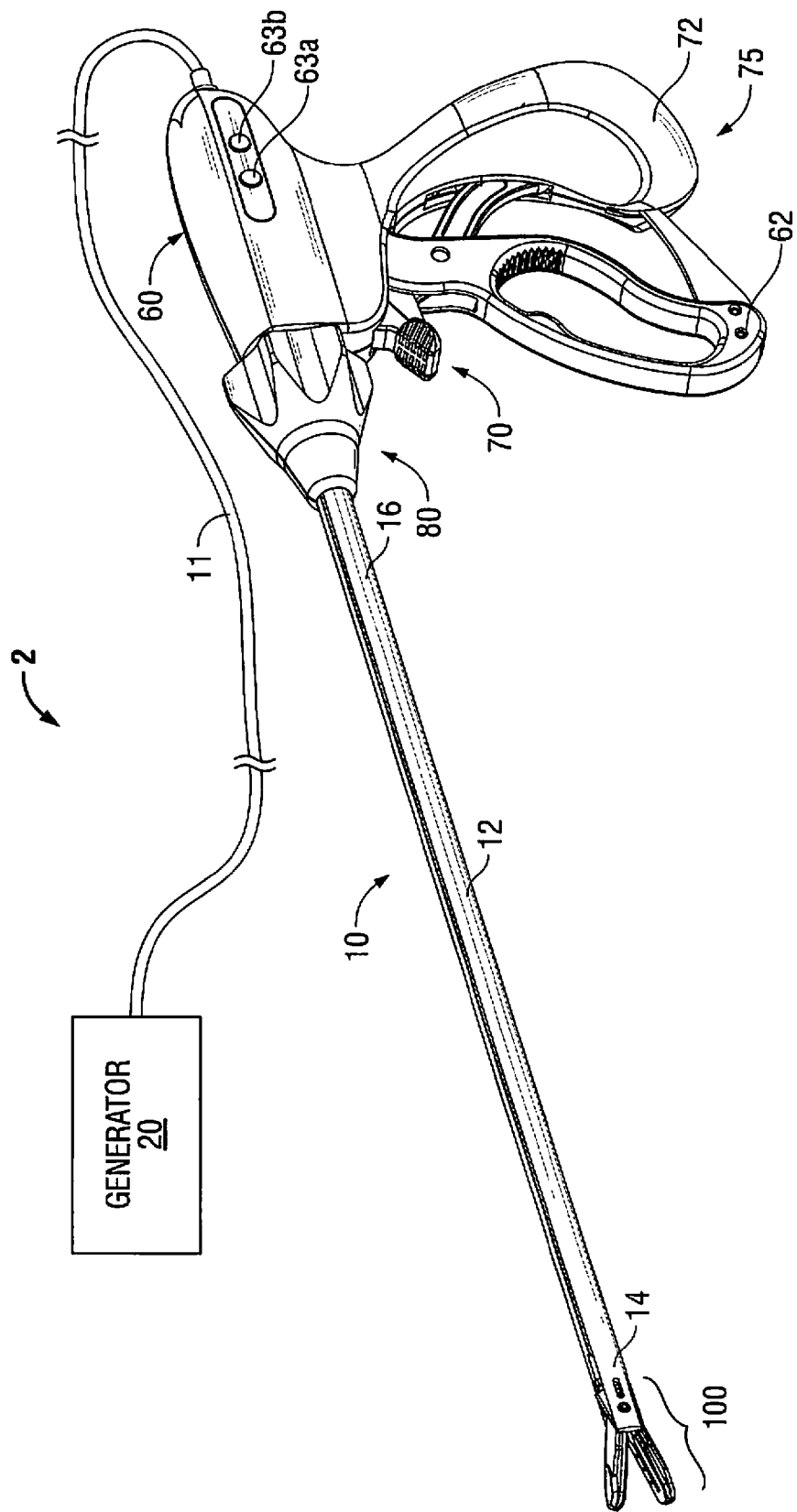
FIG. 1 is a perspective view of a tissue sealing system including a forceps and an energy generator according to one embodiment of the present disclosure.
Figure 2:
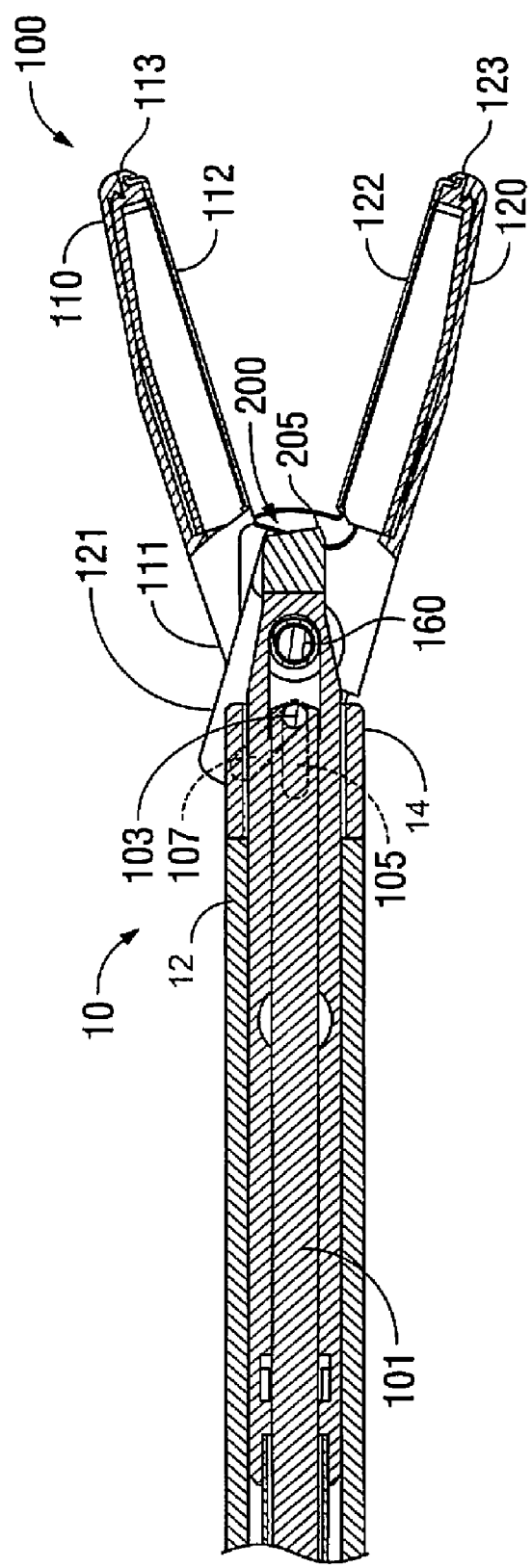
FIG. 2 is a cross-sectional view of a distal end of the forceps of FIG. 1.

Various embodiments of the present disclosure are described hereinbelow with reference to the accompanying drawings. Well-known functions or constructions are not described in detail to avoid obscuring the present disclosure in unnecessary detail. Those skilled in the art will understand that the present disclosure may be adapted for use with either an endoscopic, laparoscopic or an open instrument; however, different electrical and mechanical connections and considerations apply to each particular type of instrument. The novel aspects with respect to vessel and tissue sealing are generally consistent with respect to these designs. In the drawings and in the description which follows, the term "proximal", as is traditional, will refer to the end of the forceps that is closer to the user, while the term "distal" will refer to the end of the forceps that is further from the user.

Referring now to FIG. 1, a tissue sealing system 2 according to the present disclosure is shown including a forceps 10 coupled to a generator 20. The forceps 10 is adapted to seal tissue using ultrasound energy. The generator 20 is configured to output an electrical excitation signal to one or more ultrasound transducers within the forceps 10 at a frequency greater than 5 MHz. The forceps 10 is coupled to the generator 20 via a cable 11 adapted to transmit the appropriate energy and control signals therebetween. Various embodiments of the forceps 10 utilizing the aforementioned types of energy are discussed in more detail below.

The forceps 10 is configured to support an end effector assembly 100. Forceps 10 typically includes various conventional features (e.g., a housing 60, a handle assembly 75, a rotating assembly 80, a trigger assembly 70) that enable forceps 10 and end effector assembly 100 to mutually cooperate to grasp, seal and, if warranted, divide tissue. Forceps 10 generally includes housing 60 and handle assembly 75, which includes moveable handle 62 and handle 72 that is integral with housing 60. Handle 62 is moveable relative to handle 72 to actuate end effector assembly 100 to grasp and treat tissue. Forceps 10 also includes shaft 12 that has distal end 14 that mechanically engages end effector assembly 100 and proximal end 16 that mechanically engages housing 60 proximate rotating assembly 80 disposed at the distal end of housing 60. Rotating assembly 80 is mechanically associated with shaft 12. Movement of rotating assembly 80 imparts similar rotational movement to shaft 12 which, in turn, rotates end effector assembly 100. The shaft 12 may be either rigid or flexible. In one embodiment the end effector assembly 100 may be articulated with respect to the shaft 12. In another embodiment, the end effector assembly 100 may be disposed at a distal end of a catheter.

End effector assembly 100 includes two jaw members 110 and 120 having proximal ends 111, 121 and distal ends 113, 123. Jaw members 110 and 120 are pivotable about a post 160 and are movable from a first position wherein jaw members 110 and 120 are spaced relative to another, to a second position wherein jaw members 110 and 120 are closed and cooperate to grasp tissue therebetween. As discussed in more detail below, the end effector assembly 100 may be adapted for use with various energy sources. The jaw members 110 and 120 provide predefined closure force, which is useful to initially coapt the tissue and then in conjunction with the application of energy to permanently fuse the tissue.

The shaft 12 houses a pushrod 101 that is operatively coupled to the movable handle 62 such that when the handle 62 is moved relative to the handle 72 the pushrod 101 moves longitudinally, either proximally or distally within the shaft 12. The pushrod 101 includes a push pin 103 disposed at the distal end 16 of shaft 12. Each of the jaw members 110 and 120 includes a slot 105 and 107, respectively, disposed at the proximal ends thereof. The slots 105 and 107 are in mechanical cooperation with the push pin 103, which is adapted to move within the slots 105 and 107. The pin 103 and slots 105 and 107 operate as a cam-follower mechanical linkage. Motion of the pushrod 101 causes the pin 103 to slide within respective slots 105 and 107. The slots 105 and 107 may be angled with respect to the distal ends of the jaws members 110 and 120 such that the members 110 and 120 move either toward or away from each other as the pushrod 101 is moved longitudinally in a proximal or distal direction, respectively. In other embodiments, the actuating function of the pushrod 101 may be duplicate by a pullrod, a wire, concentrically disposed tubes and other mechanical linkages.

The forceps 10 also includes a trigger assembly 70 that advances a knife 200 disposed within the end effector assembly 100. Once a tissue seal is formed, the user activates the trigger assembly 70 to separate the tissue along the tissue seal. Knife 200 includes a sharpened edge 205 for severing the tissue held between the jaw members 110 and 120 at the tissue sealing site.

The forceps 10 further includes one or more switches 63a and 63b in communication with the generator 20 to enable and/or control the flow of energy to the end effector assembly 100. In one embodiment, the switch 63a activates flow of energy to the end effector assembly 100 and the switch 63b provides for selective energization of elements (if multiple elements/transducers are being used) as discussed in more detail below with respect to FIGS. 8 and 9.

With reference to FIG. 3, each jaw member 110 and 120 includes a sealing surface 112 and 122, respectively, disposed on an inner-facing surface thereof. Sealing surfaces 112 and 122 cooperate to seal tissue held therebetween upon the application of energy. Sealing surfaces 112 and 122 are connected to generator 20 that communicates energy through the tissue held therebetween. In particular, one or both of the jaw members 110 and 120 includes an ultrasound transducer 300 disposed on the sealing surface 112 and/or the sealing surface 122. The transducer 300 is connected via a pair of leads 301 to the generator 20 which is adapted to provide an electric signal to induce vibrations in the transducer 300. The transducer 300 may be formed from lead zirconate titanate ("PZT") or any other type of suitable ceramic perovskite material having piezoelectric properties. In another embodiment, the transducer 300 may be formed from polyvinylidene fluoride ("PVDF") or any other type of suitable polymer. The PZT provides for high heat capabilities, whereas the PVDF has lower heat capabilities than PZT, requiring low duty cycle and/or increased cooling. However, the PVDF provides higher frequency capability, which results in higher absorption rates by the tissue.

During operation, once tissue is grasped between the sealing surfaces 112 and 122, the transducer 300 is energized. This causes rapid ultrasound vibration of the transducer 300 against the tissue, which heats the tissue to a predetermined temperature and seals the tissue under applied pressure of the jaw members 110 and 120.

Each of the jaw members 110 and 120 may include a cooling cavity 310 disposed behind the transducer 300. The cooling cavity 310 is coupled to one or more inflow tubes 311a and one or more outflow tubes 311b. A coolant fluid (e.g., water, saline, silicone, etc.) or gas may be supplied to the cooling cavity 310 to remove heat generated by the vibration of the transducer 300. The gas may be a low mass gas such as helium. The coolant is supplied through the inflow tube 311a and is withdrawn through the outflow tube 311b, thereby circulating the coolant through the cavity 310. In one embodiment, the cavity 310 may simply act as an air-backing without any circulation of the coolant therethrough. In addition, the cavity 310 in combination with the coolant fluid and/or gas also reflects the ultrasound energy downward between the jaw members 110 and 120.

In one embodiment, the end effector 100 also includes a temperature sensor 320 disposed on the surface of the transducer 300. The temperature sensor 320 may be a thermocouple probe having two thermocouple wires 321 (e.g., dedicated thermocouple junction wire from about 0.001" to about 0.002") twisted together and soldered together at a junction 322. The temperature sensor 320 may provide temperature feedback to the generator 20, which may then adjust the power delivered to the transducer 300 in response to the temperature readings.

In addition to temperature feedback, the transducer 300 of the tissue sealing system 2 may also be configured to interrogate tissue to determine various tissue properties. In one embodiment, the generator 20 energizes the transducer 300 to produce an ultrasound interrogation pulse (e.g., A-mode ultrasound). The interrogation pulse may be transmitted periodically during the procedure or at any point prior to or after the commencement thereof to determine the thickness or type of tissue being grasped between the jaw members 110 and 120. The interrogation pulse may be of different frequency and amplitude than the treatment pulses used to seal tissue, therefore, supply of treatment pulses may be interrupted to transmit the interrogation pulse. More specifically, the interrogation pulse is transmitted to an interrogation transducer 313 disposed on one of the sealing surfaces 112 or 122, through the tissue and the echo of the pulse is then captured by the same transducer 313 or other feedback device or sensor (FIG. 3).

In one embodiment, where each of the jaw members 110 and 120 includes a transducer 300, the pulse may be measured as the pulse travels from one of the jaw members 110 and 120 to the other. The echo of the interrogation pulse is then transmitted to the generator 20 through a sense wire 325. Based on the transmission time of the interrogation pulse through the tissue, the generator 20 determines thickness, type, state of the tissue and/or quality of the tissue seal. The generator 20 also determines the completion of the sealing procedure based on the thickness, (e.g., based on the difference between pre-treatment and post-treatment tissue thickness or echogenicity).

Figure 6:
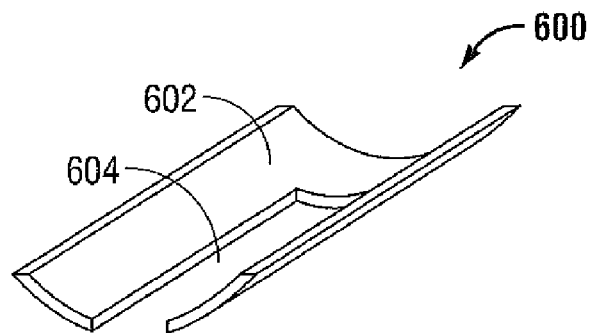
FIG. 6 is a perspective view of an ultrasound transducer according to another embodiment of the present disclosure.
Figure 7:
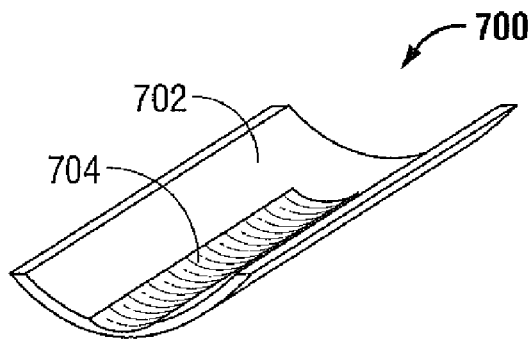
FIG. 7 is a perspective view of an ultrasound transducer according to another embodiment of the present disclosure.

FIGS. 4-7 illustrate multiple embodiments of the transducer 300. FIGS. 4 and 5 show a transducers 400 and 500 having planar tissue sealing surfaces 402 and 502, respectively. FIGS. 6 and 7 illustrate transducers 600 and 700 having a concave tissue sealing surfaces 602 and 702. The concave tissue sealing surfaces 602 and 702 have a curvilinear cross-section that define an inward curvature, which focuses the ultrasound energy toward the center of the sealing surfaces 602 and 702.

With reference to FIGS. 4 and 6, the transducers 400 and 600 include longitudinally-oriented channels 404 and 604, respectively, partially cut along a length of the transducers 400 and 600. The channels 404 and 604 extend from the proximal end to the distal end of the transducers 400 and 600. The channels 404 and 604 facilitate longitudinal reciprocation of the knife 200 along a particular cutting plane to effectively and accurately separate the tissue along a formed tissue seal.

With reference to FIGS. 5 and 7, the transducers 500 and 700 include longitudinally-oriented grooves 504 and 704, respectively, partially cut along a length of the transducers 500 and 700. The grooves 504 and 704 extend from the proximal end to the distal end of the transducers 500 and 700. The grooves 504 and 704 may also facilitate longitudinal reciprocation of the knife 200 along a particular cutting plane to effectively and accurately separate the tissue along a formed tissue seal.

Figure 8:
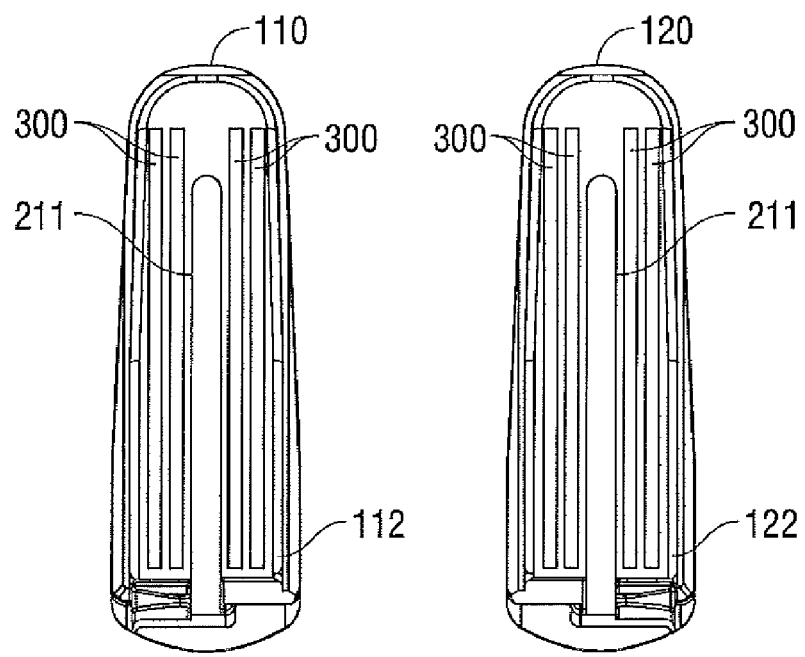
FIG. 8 is a top view of jaw members of the ultrasound end effector according to another embodiment of the present disclosure.
Figure 9:
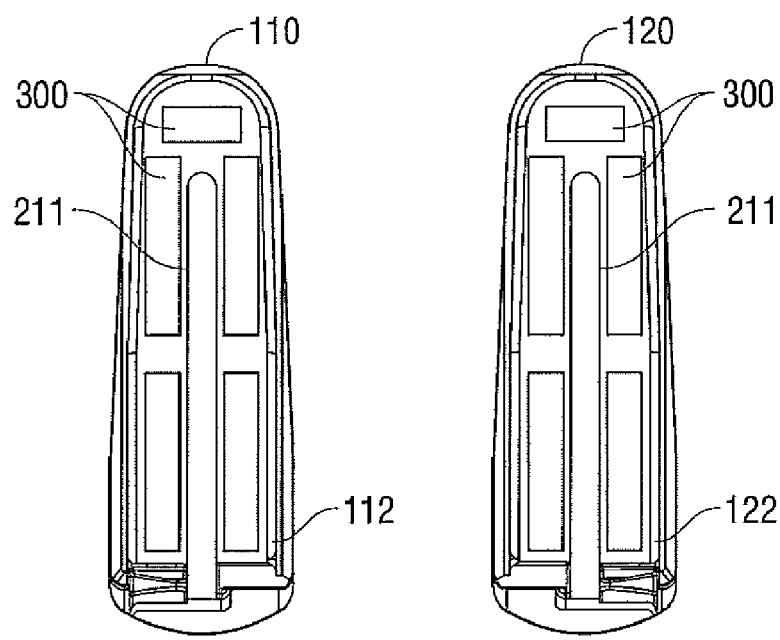
FIG. 9 is a top view of jaw members of the ultrasound end effector according to another embodiment of the present disclosure.

FIGS. 8 and 9 illustrate various embodiments of the jaw members 110 and 120 having two or more transducers 300 disposed on one or both of the sealing surfaces 112 and 122. The transducers 300 may be any of the transducers 400, 500, 600 and 700 discussed above with respect to FIGS. 4-7 and may be mounted in parallel or otherwise along the length of the respective jaw members 110 and 120. In FIG. 8, the transducers 300 are arranged longitudinally in parallel relative to each other, in pairs along each side of the sealing surfaces 112 and 122. In FIG. 9, the transducers 300 are disposed along the perimeter of the sealing surfaces 112 and 122.

Each of the transducers 300 may extend to the edge of the sealing surfaces 112 and 122. The transducers 300 may also be inset to decrease tissue heating at the edge of the sealing surfaces 112 and 122. The edge of the sealing surfaces 112 and 122 may be curved to reduce mechanical strain. The combination of reducing energy flux at the corners of the sealing surfaces 112 and 122 via curvature prevents damage to sealed tissue along the edge of the jaw members 110 and 120. In addition, extending the transducers 300 to the edge of the sealing surfaces 112 and 122 in combination with the selectively applied energy flux provides for a way to divide and/or cut sealed tissue as discussed in more detail below.

Each of the transducers 300 may be configured in a phased array for independent, simultaneous or dependent control (e.g., server-follower control). The array may include any number of transducers 300 (e.g., four) as shown in FIG. 8. In one embodiment, the array of the transducers 300 may be used to change the focus of the ultrasonic energy being applied to the tissue. More specifically, some of the transducers 300 may be activated at one frequency and a second set of transducers 300 may be activated at the same frequency offset by a desired phase angle $\theta$ causing the ultrasonic energy to spread in a manner suitable for sealing tissue. In another embodiment, the offset phase angle $\theta$ may be adjusted to deliver other tissue effects (e.g., cutting the tissue).

The switches 63a and 63b may be configured to activate the transducers 300 in a selective manner. In one embodiment, actuation of the switch 63a activates only some of the transducers 300, whereas actuation of the switch 63b activates the remaining set of the transducers 300. In another embodiment, the switches 63a and 63b may be configured to modify the phase angle $\theta$. Actuating the switch 63a delivers energy at a frequency offset by a first angle $\theta$ suitable for sealing tissue, whereas actuating the switch 63b delivers energy at a frequency offset by a second angle $\theta$ suitable for cutting tissue.

The jaw members 110 and 120 may also include a longitudinally-oriented channel 211 defined in the sealing surface 112 extending from the proximal end to the distal end thereof. The channel 211 facilitates longitudinal reciprocation of the knife 200 along a particular cutting plane to effectively and accurately separate the tissue along a formed tissue seal. The channel 211 may also be defined in the sealing surface 122 or solely disposed in only one sealing surface, e.g., sealing surface 112.

Figure 10:
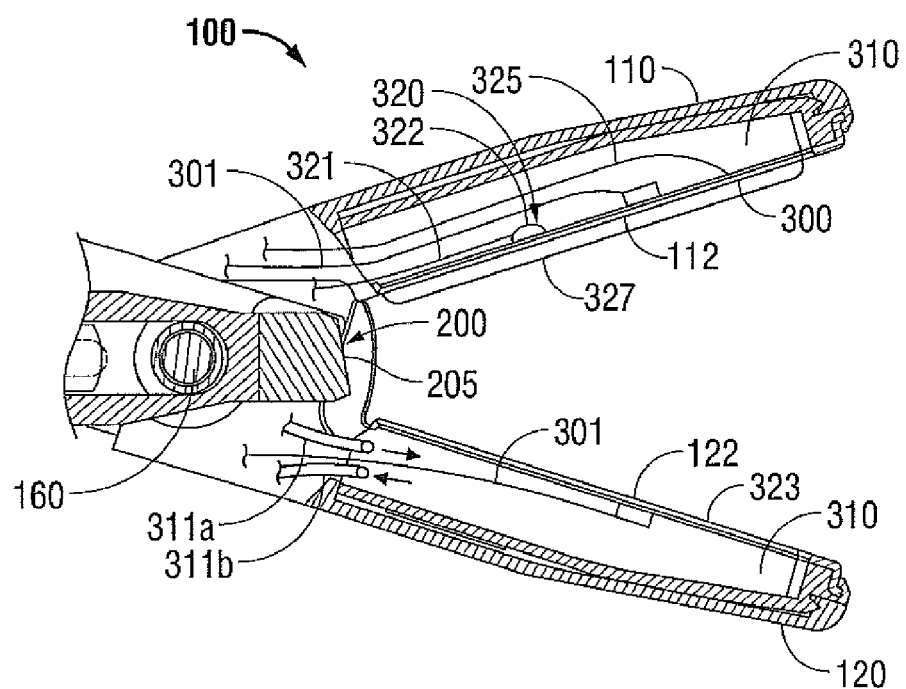
FIG. 10 is cross-sectional side view of an ultrasound end effector assembly according to one embodiment of the present disclosure.

With reference to FIG. 10, another embodiment of the end effector assembly 100 is illustrated. The transducer 300, which may be any of the transducers 400, 500, 600 and 700 discussed above with respect to FIGS. 4-7, is disposed on one of the jaws, namely the jaw member 110. The jaw member 120 includes an acoustic reflector 323 for reflecting the ultrasound energy transmitted by the transducer 300 back into the tissue grasped between the jaw members 110 and 120. In addition to the cooling cavities 310, one or both of the sealing surfaces 112 and 122 may include a coupling member 327 disposed over the transducer 300 and/or the acoustic reflector 323. The coupling member 327 may be an expandable member (e.g., balloon) to be filled with a coolant fluid (e.g., water, saline, etc.) to remove heat generated by the vibration of the transducer 300. The coolant is supplied through the inflow tube (not explicitly shown) and is withdrawn through the outflow tube (not explicitly shown), thereby circulating the coolant through the coupling member 327. In another embodiment, the coupling member 327 may be formed from a coupling gel.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ultrasound forceps for sealing tissue, comprising:
a shaft member;
an end effector assembly disposed at a distal end of the shaft member, the end effector assembly including opposing jaw members movable from a first position in spaced relation relative to one another to at least one subsequent position wherein the jaw members cooperate to grasp tissue therebetween, at least one of the jaw members includes an ultrasound transducer adapted to be coupled to an ultrasound generator so as to provide an electrical signal to the ultrasound transducer to induce at least one treatment pulse therein, the ultrasound transducer includes at least one of a longitudinally-orientated channel or a groove defined along a length thereof; and
a cutting mechanism disposed near the distal end of the shaft and operably associated with the at least one of longitudinally-oriented channel or groove so as to reciprocate the cutting mechanism through at least a portion of the ultrasound transducer.

2. The ultrasound forceps according to claim 1, where the ultrasound transducer is made from lead zirconate titanate.

3. The ultrasound forceps according to claim 1, further comprising:
a handle assembly including a first handle and a second handle, wherein the first handle is movable relative to the second handle; and
a pushrod operatively coupled at one end to the handle assembly and to the end effector assembly, wherein longitudinal movement of the pushrod moves the jaw members from the first position to the at least one subsequent position.

4. The ultrasound forceps according to claim 1, further comprising:
an actuator operatively connected to the shaft member for selectively advancing the cutting mechanism from a first position wherein the cutting mechanism is disposed proximal to tissue held between the jaw members to at least one subsequent position wherein the cutting mechanism is disposed distal to tissue held between the jaw members.

5. The ultrasound forceps according to claim 1, wherein the ultrasound transducer includes a planar tissue sealing surface.

6. The ultrasound forceps according to claim 1, wherein the ultrasound transducer includes a concave tissue sealing surface.

7. The ultrasound forceps according to claim 1, wherein the ultrasound transducer includes a temperature sensor, which is coupled to the ultrasound generator and is adapted to provide temperature feedback thereto.

8. The ultrasound forceps according to claim 1, wherein the ultrasound generator is adapted to energize the ultrasound transducer to produce an ultrasound interrogation pulse that is of different frequency and amplitude from the at least one treatment pulse.

9. A method for sealing tissue, comprising the steps of:
grasping tissue between opposing jaw members movable from a first position in spaced relation relative to one another to at least one subsequent position wherein the jaw members cooperate to grasp tissue therebetween, at least one of the jaw members including an ultrasound transducer, having at least one of a longitudinally-orientated channel or a groove defined along a length thereof;
supplying an electrical signal to the ultrasound transducer to induce vibrations therein to seal tissue; and
reciprocating a cutting mechanism operably associated with the at least one of longitudinally-oriented channel or groove through at least a portion of the ultrasound transducer.

10. The method according to claim 9, further comprising the step of:
energizing the ultrasound transducer to produce an ultrasound interrogation pulse that is of different frequency and amplitude from a treatment pulse.

11. An ultrasound forceps for sealing tissue, comprising:
a shaft member;
an end effector assembly disposed at a distal end of the shaft member, the end effector assembly including opposing jaw members movable from a first position in spaced relation relative to one another to at least one subsequent position wherein the jaw members cooperate to grasp tissue therebetween, each of the jaw members includes a plurality of ultrasound transducers coupled to an ultrasound generator adapted to provide an electrical signal to the plurality of ultrasound transducers to induce at least one treatment pulse therein, wherein at least one of the plurality of the ultrasound transducers includes at least one of a longitudinally-orientated channel or a groove defined along a length thereof; and
a cutting mechanism disposed near the distal end of the shaft and operably associated with the at least one of a longitudinally-orientated channel or a groove so as to reciprocate the cutting mechanism through at least a portion of at least one of the plurality of the ultrasound transducers.

12. The ultrasound forceps according to claim 11, wherein the plurality of ultrasound transducers are controlled in at least one of independent, simultaneous or dependent manner.

* * * * *